(12) United States Patent
Spear

(10) Patent No.: US 7,971,744 B2
(45) Date of Patent: Jul. 5, 2011

(54) FOAM VESSEL FOR CRYOGENIC FLUID STORAGE

(76) Inventor: Jonathan D Spear, San Francisco, CA (US)

( * ) Notice: Subject to any disclaimer, the term of this patent is extended or adjusted under 35 U.S.C. 154(b) by 479 days.

(21) Appl. No.: 11/424,953

(22) Filed: Jun. 19, 2006

(65) Prior Publication Data

US 2006/0289545 A1 Dec. 28, 2006

Related U.S. Application Data

(60) Provisional application No. 60/693,827, filed on Jun. 24, 2005.

(51) Int. Cl.
*F17C 13/00* (2006.01)
(52) U.S. Cl. ............... 220/560.12; 62/45.1; 220/901
(58) Field of Classification Search ............ 62/45.1; 220/560.12, 901
See application file for complete search history.

(56) References Cited

U.S. PATENT DOCUMENTS

| | | | | |
|---|---|---|---|---|
| 3,019,937 | A * | 2/1962 | Morrison | 220/560.12 |
| 3,924,039 | A * | 12/1975 | Smith, Jr. | 428/119 |
| 3,929,247 | A | 12/1975 | Borup | |
| 3,970,210 | A | 7/1976 | Katsuta | |
| 4,089,285 | A | 5/1978 | Okamoto | |
| 4,109,823 | A | 8/1978 | Ffooks, Jr. | |
| 4,933,040 | A | 6/1990 | Wesley, Jr. | |
| 5,150,812 | A | 9/1992 | Adams | |
| 6,093,468 | A * | 7/2000 | Toms et al. | 428/67 |
| 6,206,223 | B1 * | 3/2001 | Wicker | 220/375 |

* cited by examiner

*Primary Examiner* — Anthony Stashick
*Assistant Examiner* — Elizabeth Volz
(74) *Attorney, Agent, or Firm* — PatentBest; Andrew McAleavey

(57) ABSTRACT

Cryogenic storage and separator vessels made of polyolefin foams are disclosed, as are methods of storing and separating cryogenic fluids and fluid mixtures using these vessels. In one embodiment, the polyolefin foams may be cross-linked, closed-cell polyethylene foams with a density of from about 2 pounds per cubic foot to a density of about 4 pounds per cubic foot.

18 Claims, 4 Drawing Sheets

FOAM VESSEL FOR CRYOGENIC FLUID STORAGE

CROSS-REFERENCE TO RELATED APPLICATIONS

Priority is claimed to U.S. Provisional Application No. 60/693,827, filed Jun. 24, 2005 and entitled "Foam Vessel for Liquid Nitrogen."

STATEMENT REGARDING FEDERALLY FUNDED RESEARCH AND DEVELOPMENT

This invention was made with Government support under contract No. DE-AC03-76SF00098 awarded by the Department of Energy. The Government has certain rights in this invention.

BACKGROUND OF THE INVENTION

1. Field of the Invention

The invention relates to foam vessels for cryogenic fluid storage and separation.

2. Description of Related Art

Cryogenic fluids, such as liquid nitrogen, liquid oxygen, and liquid hydrogen have found a vast number of scientific and other applications. These fluids are extremely cold (liquid nitrogen, for example, boils at about $-196°$ C.) and are used, for example, in biological specimen preparation and preservation, x-ray crystallography sample preparation, environmental testing, and general refrigeration, to name a few. Liquid nitrogen, in particular, is nearly ubiquitous in most modern laboratories.

Storing cryogenic fluids poses its own set of problems, not the least of which is minimizing heat transfer into and out of the fluid. The original cryogenic storage vessels were the work of Sir James Dewar, and are named in his honor. The classic Dewar is a double vessel with a glass inner wall, an outer wall, and an evacuated space between the inner and outer walls that reduces heat transfer by conduction. The glass may be silvered to reduce heat transfer by radiation, and an outer layer of metal is sometimes provided.

There are four major problems with classic Dewars. First, if the Dewar is dropped during handling, there is a risk that the glass will shatter. Second, the glass material has a large thermal mass, which means that a relatively large amount of cryogenic fluid will boil off and be lost in cooling the Dewar to the appropriate temperature when fluid is first placed in the Dewar for storage. Third, the cost of a traditional Dewar is high. (For example, at the time of writing, a 600 mL Dewar sold by Hampton Research of Aliso Viejo, Calif. has a retail price of $197.) Finally, the classic Dewar is not necessarily easy to handle.

Occasionally, thin-walled polystyrene foam containers, such as STYROFOAM® coffee cups, have been used to hold liquid nitrogen temporarily during use. However, polystyrene vessels of this type often cause the liquid nitrogen to boil off relatively rapidly. Moreover, these sorts of vessels are not mechanically robust and tend to fail easily.

SUMMARY OF THE INVENTION

One aspect of the invention relates to a cryogenic fluid vessel. The cryogenic fluid vessel comprises a sidewall and a bottom defining a cryogenic fluid compartment having an opening. The sidewall and bottom are comprised of a cross-linked, closed-cell polyolefin foam having a density of at least about 2 pounds per cubic foot. Inner faces of the sidewall and bottom are arranged so as to contact a cryogenic fluid placed in the cryogenic fluid compartment.

Another aspect of the invention relates to a method of storing a cryogenic fluid or cryogenic mixture. The method comprises placing the cryogenic fluid or cryogenic mixture into a vessel such that the cryogenic fluid is directly in contact with a portion of the vessel comprised of a cross-linked polyolefin foam having a density of at least about 2 pounds per cubic foot.

A further aspect of the invention relates to a cryogenic fluid storage vessel. The cryogenic fluid storage vessel comprises a cross-linked, closed-cell polyolefin foam in which is defined a cryogenic fluid compartment with an opening in a top face of the polyolefin foam. The thickness of polyolefin foam between an inner face of the cryogenic fluid compartment and an outer face of the polyolefin foam is at least about 0.5 inches. The cryogenic fluid storage vessel also comprises at least one handling feature defined in the polyolefin foam. The density of the polyolefin foam is at least about 2 pounds per cubic foot.

Other aspects, features, and advantages of the invention will become clear from the description that follows.

BRIEF DESCRIPTION OF THE DRAWINGS

The invention will be described with respect to the following drawing figures, in which like numerals represent like features throughout the views, and in which.

DETAILED DESCRIPTION

Cross-linked, closed-cell polyolefin foams have been found by the present inventor to be suitable materials for cryogenic vessels. Several characteristics of polyolefin foams make them advantageous for use as cryogenic vessels: they can be fabricated easily into appropriate shapes by molding, casting or otherwise forming the foam from monomer or polymer, or by machining finished blocks; their cell structure is typically fine enough to contain, for example, liquid nitrogen, without leaking; they are durable enough to withstand repeated exposures to cryogenic temperatures; they are largely non-reactive; and they typically have both a low thermal conductivity and a low volumetric heat capacity. Additionally, vessels made of polyolefin foam can withstand moderate physical handling without mechanical failure.

As used here, the term "polyolefin foam" refers to polyethylene foam, polypropylene foam, polyethylene-polypropylene mixtures and copolymers, and foams that contain a mixture or copolymer of olefin monomer and other monomers, to the extent that the mixed foams have at least some of the favorable characteristics noted above. In addition to the polymer or polymers that comprise the polyolefin foam, such foams may also have any additives known in the art. For example, the foams may include softeners, coloring agents, stabilizers, preservatives, and fillers. As one example, ethyl vinyl alcohol (EVA) is sometimes included in polyethylene foam as a softener.

Polyolefin foams are typically provided in a variety of densities. In selecting the density of a polyolefin foam that is to be used for a cryogenic vessel, one should seek to balance the mechanical and thermal properties of the material. If the foam is not very dense, it may not have advantageous mechanical properties; if the foam is too dense, it will have higher thermal conductivity. For embodiments of the present invention, it has been found that polyolefin foam with a density of at least about 2 pounds per cubic foot is suitable, and that densities in the range of about 2 pounds to slightly greater than about 4 pounds may be particularly advantageous. However, in some embodiments, it is anticipated that foams with densities of 6-8 pounds per cubic foot could be used.

Figure 1:
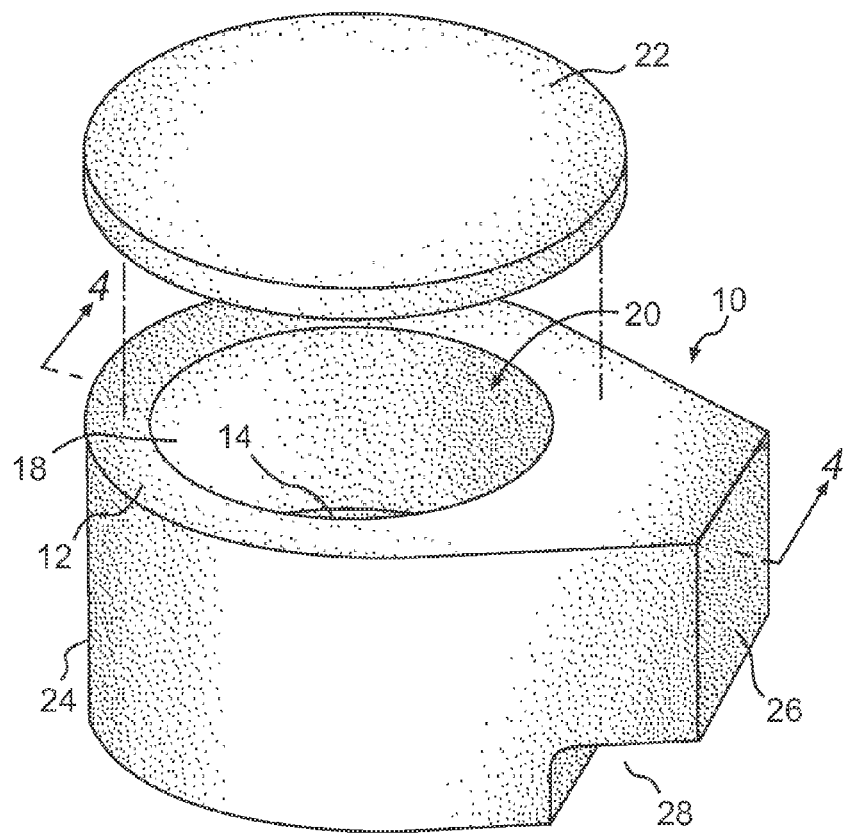
FIG. 1 is a perspective view of a cryogenic storage vessel according to one embodiment of the invention.
Figure 4:
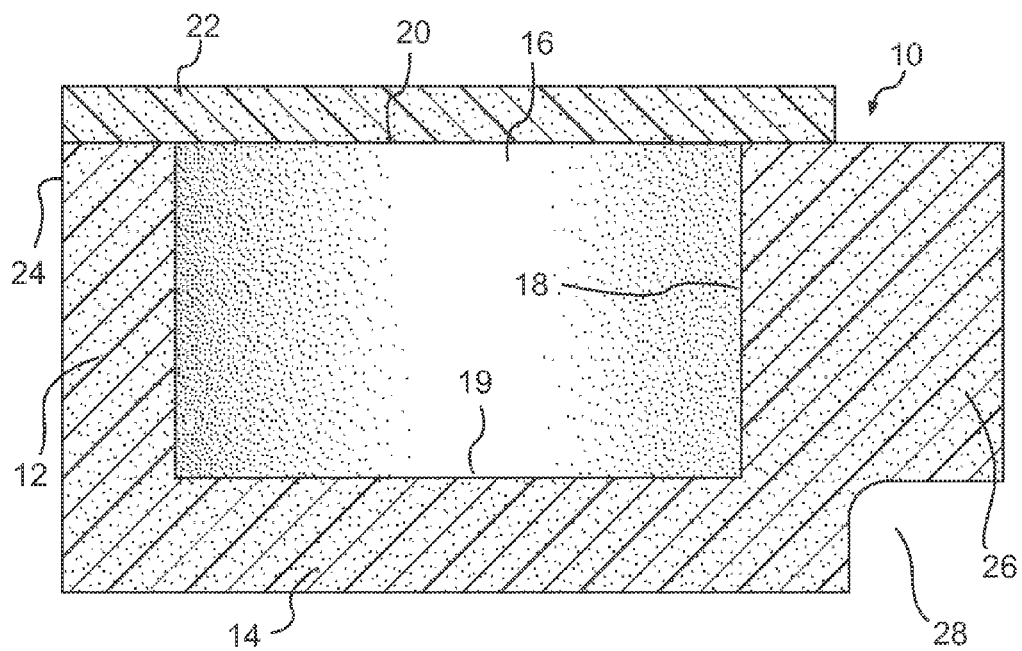
FIG. 4 is a sectional view of the cryogenic storage vessel of FIG. 1, taken through Line 4-4 of FIG. 1.

Cryogenic storage vessels according to embodiments of the present invention may take many forms, depending on the volume of cryogenic fluid that is to be contained, the manner in which the vessel will be handled, and the length of time the vessel is designed to contain the cryogenic fluid, among other factors. FIG. 1 is a perspective view of a cryogenic storage vessel, generally indicated at 10, according to one embodiment of the invention. FIG. 4 is a cross-sectional view of the storage vessel 10.

The storage vessel 10 has a sidewall 12 and a bottom 14 that define a compartment 16 into which cryogenic fluid, such as liquid nitrogen, may be placed for storage. More particularly, the inner face 18 of the sidewall 12 and the inner face 19 of the bottom 14 define the compartment 16 and are designed to be in direct contact with the cryogenic fluid. The compartment 16 has a single opening 20, in this case located at its top.

As shown best in FIG. 4, both the sidewall 12 and bottom 14 have a substantial thickness, such that the foam acts as an insulator to prevent heat transfer into the cryogenic fluid. A removable lid 22, also of polyolefin foam, is round, sized to about the same diameter as the opening 20 of the compartment 16, and may be placed over the opening 20 to reduce heat transfer through the opening 20. In the view of FIG. 4, the removable lid 22 is covering the opening 20.

Figure 2:
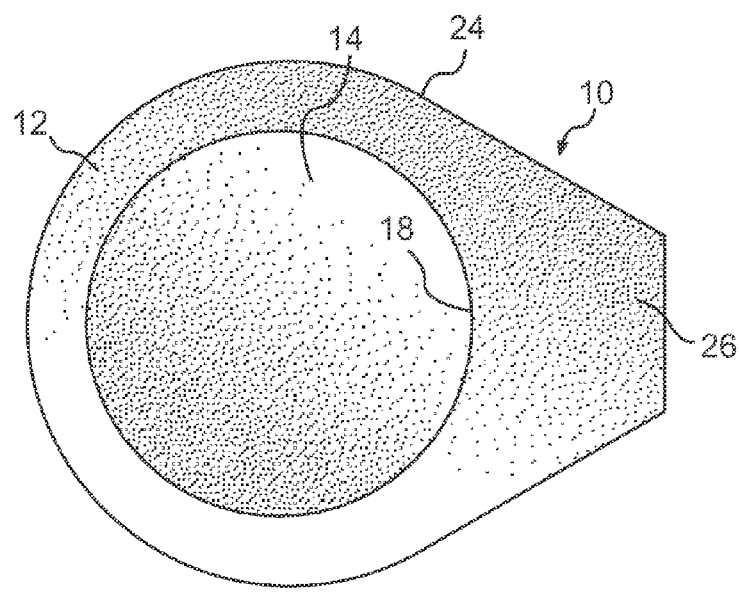
FIG. 2 is a top plan view of the cryogenic storage vessel of FIG. 1.
Figure 3:
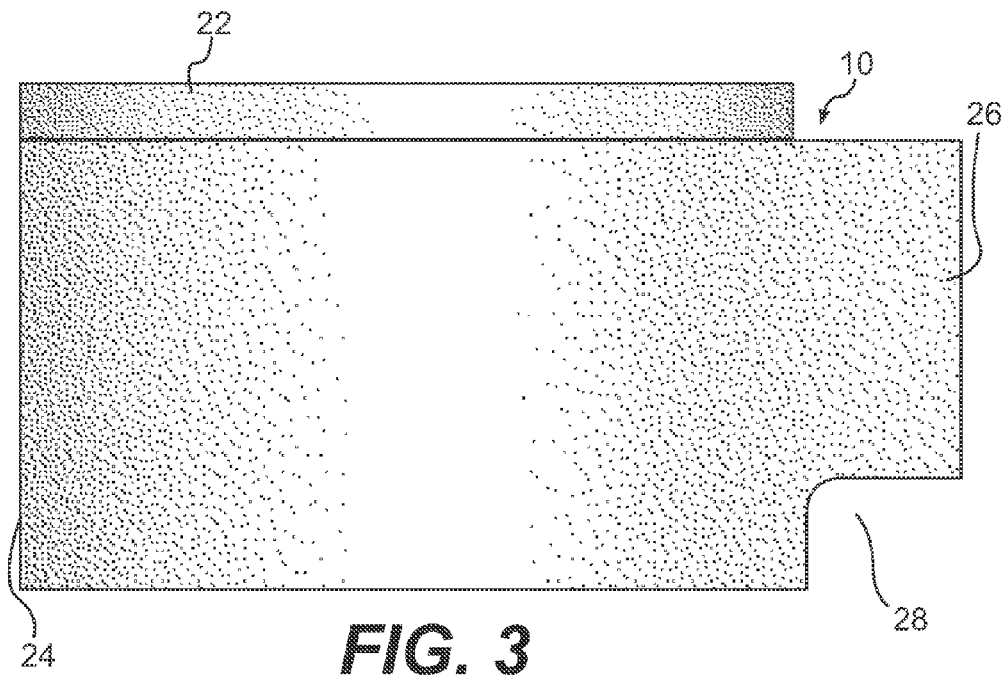
FIG. 3 is a side elevational view of the cryogenic storage vessel of FIG. 1.

As shown in FIGS. 2 and 3, which are, respectively, a top plan view and a side elevational view of the storage vessel 10, the storage vessel 10 also includes features that make it easier to handle. In this embodiment, the storage vessel 10 has an overall shape somewhat similar to a teardrop, which can be seen in FIGS. 1 and 2. Integral with outer face 24 of the sidewall 12, is a solid portion 26, into which a recess 28 has been cut. During use, the recess 28 serves as a handle.

The recess 28 is merely one example of the type of feature that may be used for handling. In some embodiments, there may be several solid portions 26, for example, one on each side, with multiple recesses 28 or other handling features. Moreover, one particular advantage of a polyolefin foam vessel according to the present invention is that a user can easily machine or cut any needed handling feature from any portion of the storage vessel 10, provided that its thermal and mechanical properties for the desired application are not compromised. For example, features that may be included in the storage vessel 10 or machined into the storage vessel 10 include handles, hooks, holes and channels of various configurations.

Figure 5:
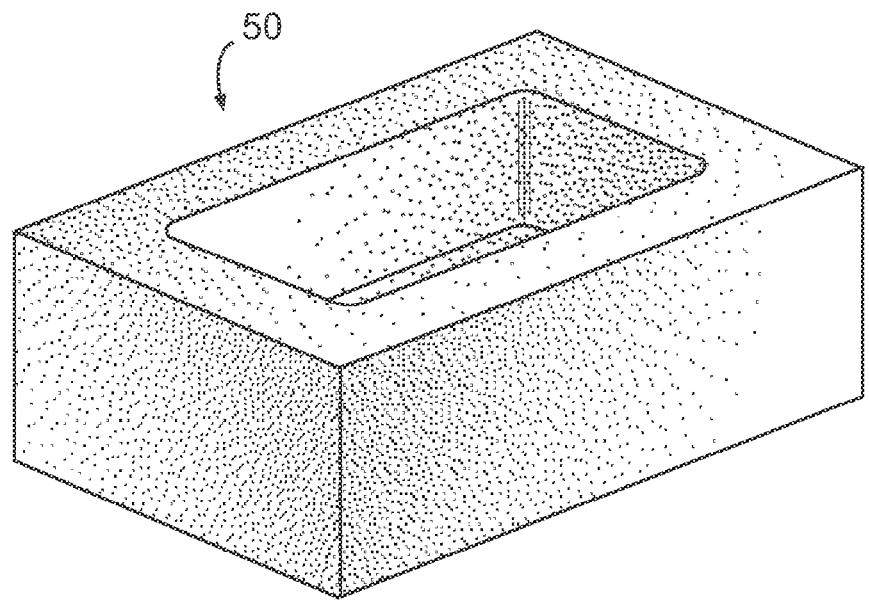
FIGS. 5 and 6 are perspective views of cryogenic storage vessels according to other embodiments of the invention.
Figure 6:
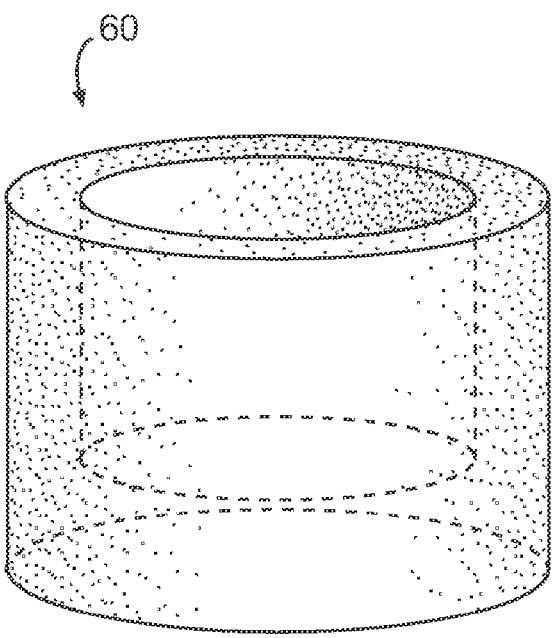

The relative sizes and thicknesses of the sidewall 12 and the bottom 14 may vary, as may the height-to-width aspect ratio of the storage vessel 10. Some embodiments of storage vessels according to embodiments of the invention may be tall and thin; others may be wide and shallow. FIGS. 5 and 6 are perspective views of cryogenic storage vessels 50 and 60 of other shapes. Storage vessel 60 is cylindrical and tall, while storage vessel 50 is relatively flat and rectangular.

If a cryogenic storage vessel is to be made with a size that is larger than the largest available contiguous block of polyolefin foam, the vessel may be made in sections that are bonded or otherwise joined together to make a contiguous whole. One technique is to stack several layers of foam together and bond or otherwise join them to form a larger block. A cryogenic storage vessel can then be machined out of the larger block. Another technique is to cut an intermediate layer into a desired shape and then bond or otherwise join pieces of foam around it to form a complete cryogenic storage vessel.

Figure 7:
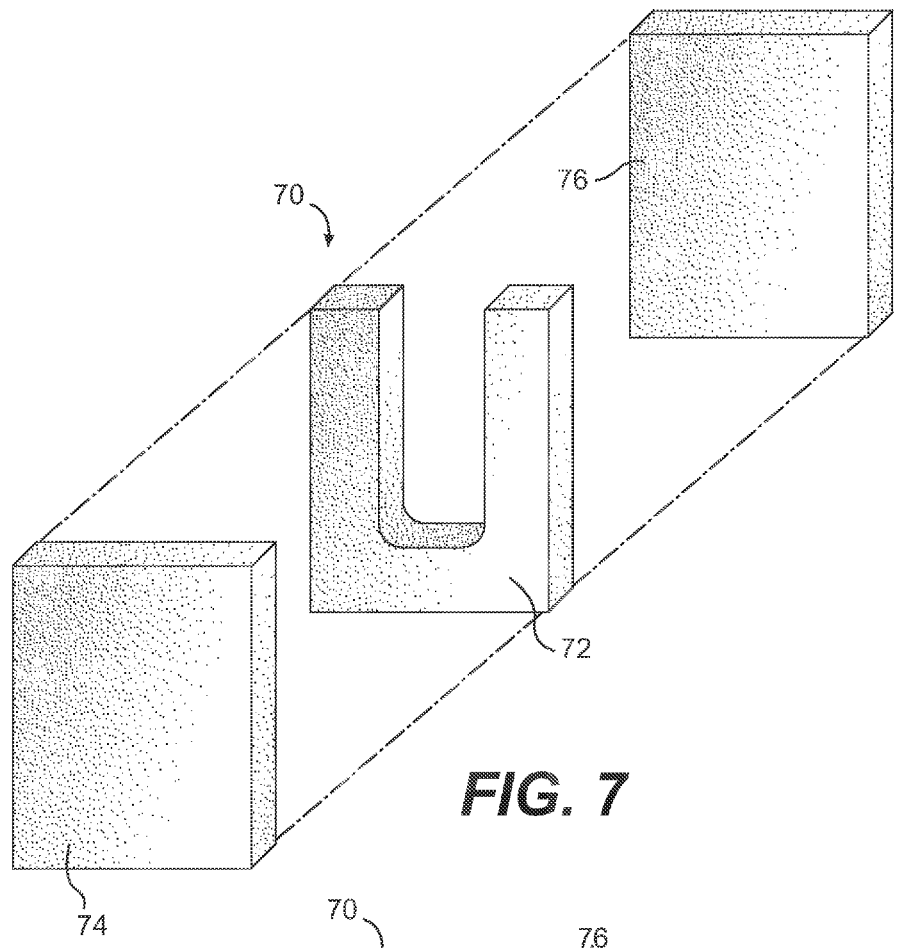
FIG. 7 is an exploded perspective view of a cryogenic storage vessel constructed in several segments.
Figure 8:
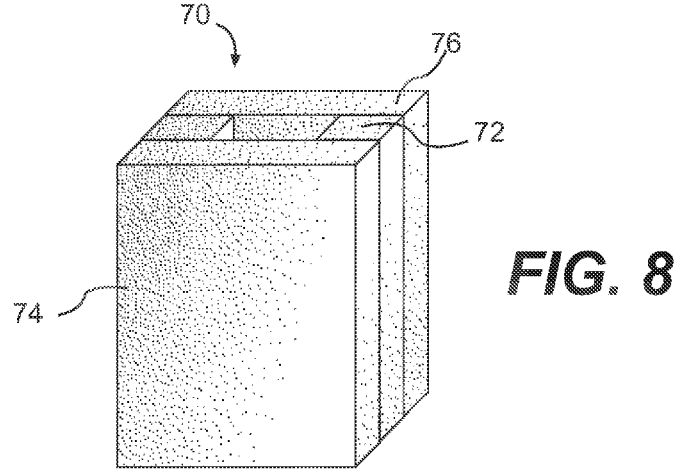
FIG. 8 is an assembled perspective view of the cryogenic storage vessel of FIG. 7.

The latter technique for assembling cryogenic storage vessels is illustrated in FIG. 7, an exploded perspective view of a cryogenic storage vessel 70, and FIG. 8, an assembled perspective view of the cryogenic storage vessel 70. As shown in FIG. 7, the cryogenic vessel 70 is comprised of three sections: a central, U-shaped section 72 and two sidewall sections 74, 76. The two sidewall sections 74, 76 are bonded to the U-shaped section 72. Essentially any adhesive may be used in the bonding, although spray adhesives have been found to be particularly suitable. For example, the line of spray (aerosol) adhesives from 3M (St. Paul, Minn.) has been found to be suitable, including spray adhesive 76, spray adhesive 77, and spray adhesive 90. For a secure bond, it may be helpful to coat both surfaces that are to be bonded together. Depending on the adhesive, clamping may or may not be required. Additionally, if a cryogenic vessel 70 is much taller than it is wide, it may be helpful to make the base of the container slightly wider than the top of the container, in order to ensure stability.

Regardless of the size or shape of the cryogenic vessel 10, 50, 60, 70, the sidewall and bottom should be thick enough to provide adequate insulation. If liquid nitrogen is the cryogenic fluid, a thickness of about 0.5 inches to about 1 inch has been found to be adequate. If a lid 22 is provided, the lid may have a thickness in that same range.

Polyolefin cryogenic storage vessels 10, 50, 60, 70 according to embodiments of the invention are generally capable of direct contact with cryogens like liquid nitrogen. However, in some cases, thin layers of insubstantial thermal mass may be added to the polyolefin material. For example, a cryogenic storage vessel 10, 50, 60, 70 may be painted. In that case, the cryogen would be in direct contact with the paint or other thin layer.

Although certain examples have been given with liquid nitrogen as the cryogenic fluid, other cryogenic fluids and other cold mixtures may be stored. For example, liquid oxygen and other liquefied gases could be stored, as could solid carbon dioxide (i.e., dry ice) and mixtures of dry ice and water or other fluids. The only limitation is that it may not be desirable to store a fluid, cryogenic or otherwise, that is known to react with or dissolve cross-linked polyolefin. It will also be realized that some solvents tend to swell the matrix of a cross-linked polymer without dissolving the polymer; these may be stored, although it may be advisable to do so only for relatively short periods of time.

Storage is not the only use to which vessels according to embodiments of the invention may be put. As one example, when liquid nitrogen or another liquefied gaseous cryogen is first drawn from a larger tank, the liquid may be expelled along with a large, undesirable volume of the gas. Polyolefin vessels may be used as separators to separate the undesirable gas from the desirable cryogenic fluid. For example, a cryogenic separator vessel could be constructed in the shape of a funnel with high sidewalls. Such a vessel would allow liquid cryogen to pass into another vessel while protecting the user from the gas that is expelled with the fluid.

Other details of the construction of storage vessels 10, 50, 60, 70 according to embodiments of the invention will be set forth in the following examples.

Example 1

Polyethylene Foam Storage Vessel from Block Material

A rectangular foam block with dimensions of 6 inches by 20 inches by four inches was purchased from Elephant Pharmacy (Berkeley, Calif., United States). A cylindrical cavity was machined in the block using a Bridgeport vertical milling machine with an end mill and a rotary table. Liquid nitrogen was poured into the cavity and it was found to be a good insulator at cryogenic temperatures. The material, which was labeled for use in various exercise routines, was later identified as cross-linked polyethylene foam.

Example 2

Polyethylene Foam Storage Vessel from Sheet Material

A 4-inch by 48-inch by 72-inch sheet of cross-linked polyethylene foam Y40 with purple colorant having a density of four pounds per cubic foot was purchased from RAM Technologies (Mukilteo, Wash., United States). The sheet of foam was manufactured by the Youngbo Chemical Company, Ltd. of South Korea. A piece of foam having the general shape shown in FIG. 1 was cut from the sheet, and a compartment was milled into the cut piece using a Bridgeport vertical milling machine with an end mill and a rotary table. The compartment had a diameter of about 5 inches, and a depth of about 3 inches with a one-inch sidewall and bottom. A recess was included, so that the finished container had the shape shown in FIG. 1. The resulting vessel was found to be a good carrier for liquid nitrogen.

In empirical observations of both foam cryogenic vessels as compared with Dewars of approximately the same volumes using liquid nitrogen, it was found that less liquid nitrogen boiled off from the foam containers during initial filling, presumably because of the lower thermal mass of the foam containers. Both were found to be suitable vessels for storage of liquid nitrogen for at least short-term periods of less than one day.

Theoretically, the thermal insulation of a Dewar may outperform the insulation of a foam cryogenic storage vessel, because the evacuated layer between the inner and outer faces of the Dewar prevents heat transmission by conduction and the Dewar's silvered or reflective surfaces will reduce transmission by radiation. However, foam cryogenic storage vessels may have particular advantages over a Dewar with a small volume and a relatively large opening. While Applicant does not intend to be bound by any particular theory, it is believed that if a Dewar has a small volume and a relatively large opening, heat transfer across the opening becomes significant and the Dewar will thus lose the advantages otherwise conferred by its insulation.

Example 3

Polyethylene foam Storage Vessel from Bonded Sections

A supply of Youngbo closed-cell polyethylene foam with a density of 2 pounds per cubic foot was purchased from a foam supplier. A U-shaped central section resembling section 72 of FIG. 7 was rough cut from a three inch thick sheet of foam. Two side sections were also rough cut from two inch thick sheet of foam. Finish cuts on all three sections were made using a band saw in order to produce smooth surfaces. After machining, the U-shaped central section was approximately 14.5 inches long, three inches deep, and was tapered, such that it had a width of approximately five and one eighth inches at the top and six and five eighths inches at the bottom. The two side sections had matching lengths, thicknesses that increased from one inch at the top to approximately one and seven eighths inches at the bottom, and widths that increased from five and one eighth inches at the top to six and five eighths inches at the bottom. The central section and two side sections were joined by coating all of the interfacing surfaces with 3M aerosol adhesive to form a unitary cryogenic storage vessel approximately 14.5 inches tall, with a width and depth of five and one eighth inches at the top and a width and depth of six and five eighths inches at the bottom. The taper, broader base, and overall semi-pyramidal shape of the storage vessel were intended to prevent it from tipping when in use.

The construction methods and techniques illustrated in the above examples are advantageous because they allow cryogenic storage vessels to be made in arbitrary sizes from stock materials. However, as those of skill in the art will realize, in some embodiments, polyolefin material may be formed in the shape of a storage vessel using conventional molding, blowing and/or other forming techniques, instead of machining or assembling the vessel from stock materials.

While the invention has been described with respect to certain embodiments, the description is intended to be exemplary, rather than limiting. Modifications and changes may be made within the scope of the invention, as set forth in the following claims.

What is claimed is:

1. A cryogenic fluid vessel, comprising:
 a sidewall and bottom defining a cryogenic fluid compartment having an opening, the sidewall and bottom being entirely comprised of a cross-linked, closed-cell polyolefin foam having a density of at least about 2 pounds per cubic foot and a sidewall thickness of at least about 0.5 inches;
 wherein inner faces of the sidewall and bottom are arranged so as to contact and store a cryogenic fluid placed in the cryogenic fluid compartment.

2. The cryogenic fluid vessel of claim 1, wherein the cross-linked polyolefin foam has a density of about 2 pounds per cubic foot to about 4 pounds per cubic foot.

3. The cryogenic fluid vessel of claim 1, further comprising a lid sized and adapted to close the opening.

4. The cryogenic fluid vessel of claim 1, wherein the cryogenic fluid vessel consists essentially of the sidewall and the bottom defining the cryogenic fluid compartment.

5. A method of storing a cryogenic fluid, comprising placing the fluid in the cryogenic fluid vessel of claim 1.

6. The cryogenic fluid vessel of claim 1, wherein the cryogenic fluid is liquid nitrogen.

7. The cryogenic fluid vessel of claim 1, wherein the cross-linked polyolefin foam is cross-linked polyethylene foam.

8. The cryogenic fluid vessel of claim 7, wherein the cross-linked polyethylene foam has a density of 4 pounds per square foot.

9. The cryogenic fluid vessel of claim 1, further comprising a handling feature.

10. The cryogenic fluid vessel of claim 9, wherein the handling feature is a recess formed in a solid portion contiguous with the sidewall.

11. A method of storing a cryogenic fluid or cryogenic mixture, comprising:
placing the cryogenic fluid or cryogenic mixture into a vessel entirely comprised of a cross-linked, closed-cell polyolefin foam having a density of at least about 2 pounds per cubic foot and a wall thickness of at least about 0.5 inches such that the cryogenic fluid is contained by and in contact with a compartment within the vessel.

12. The method of claim 11, further comprising covering the vessel with a lid.

13. The method of claim 11, wherein the cross-linked polyolefin foam is cross-linked polyethylene foam.

14. The method of claim 11, wherein the cross-linked polyolefin foam has a density in the range of from about 2 pounds per cubic foot to about 4 pounds per cubic foot.

15. A cryogenic fluid storage vessel, comprising:
a cross-linked, closed-cell polyolefin foam in which is defined a cryogenic fluid compartment with an opening, the thickness of polyolefin foam between an inner face of the cryogenic fluid compartment and an outer face of the polyolefin foam being at least about 0.5 inches, the entirety of the cryogenic fluid storage vessel being comprised of the polyolefin foam, the polyolefin foam being constructed and arranged such that inner faces of the sidewall and bottom are arranged so as to contact and contain a cryogenic fluid placed in the cryogenic fluid compartment; and
at least one handling feature defined in the polyolefin foam;
wherein the density of the piece of polyolefin foam is in the range from about 2 pounds per cubic foot to about 4 pounds per cubic foot; and
wherein the polyolefin foam is selected from the group consisting of polyethylene foam, polypropylene foam, polyethylene-polypropylene foam mixtures, and polyethylene-polypropylene copolymer foams.

16. In combination:
a cryogenic fluid storage vessel consisting of a cross-linked, closed-cell polyolefin foam with a density of at least about 2 pounds per cubic foot in which is defined a cryogenic fluid compartment with an opening, the thickness of polyolefin foam between an inner face of the cryogenic fluid compartment and an outer face of the polyolefin foam being at least about 0.5 inches, the entire inner face of the cryogenic fluid compartment being comprised of the polyolefin foam, at least one handling feature being defined in the polyolefin foam,
wherein the polyolefin foam is selected from the group consisting of polyethylene foam, polypropylene foam, polyethylene-polypropylene foam mixtures, and polyethylene-polypropylene copolymer foams; and
a cryogenic fluid or cryogenic fluid mixture in the cryogenic fluid compartment.

17. The combination of claim 16, wherein the polyolefin foam is polyethylene foam with a density in the range of about 2 pounds to about 4 pounds per cubic foot.

18. The combination of claim 16, wherein the handling feature is a recess formed in a solid portion of the polyolefin foam.

* * * * *